United States Patent [19]

Büchel et al.

[11] 4,134,725

[45] Jan. 16, 1979

[54] PROCESS FOR THE PRODUCTION OF GRANULES

[75] Inventors: Urs Büchel, Oberwil; Hans Mollet, Reinach, both of Switzerland

[73] Assignee: Ciba-Geigy Corporation, Ardsley, N.Y.

[21] Appl. No.: 798,553

[22] Filed: May 19, 1977

[30] Foreign Application Priority Data

May 25, 1976 [CH] Switzerland .......................... 6570/76

[51] Int. Cl.² ............................................. C09B 67/00
[52] U.S. Cl. ......................................... 8/79; 264/117; 71/DIG. 1; 252/543; 252/174; 427/212
[58] Field of Search ............................... 264/117; 8/79; 71/DIG. 1; 252/543, 174; 427/212

[56] References Cited

U.S. PATENT DOCUMENTS

| | | | |
|---|---|---|---|
| 3,803,283 | 4/1974 | Takewell et al. | 264/117 |
| 3,872,200 | 3/1975 | Tokito et al. | 264/117 |
| 3,882,217 | 5/1975 | Banham et al. | 264/117 |

OTHER PUBLICATIONS

Chemical Engineering, Dec. 4, 1967, McGraw-Hill Publishing Co., New York, New York.

Primary Examiner—Robert F. White
Assistant Examiner—James R. Hall
Attorney, Agent, or Firm—Edward McC. Roberts; Michael W. Glynn

[57] ABSTRACT

An improved process for the production of granules, comprising application of a granulating liquid to a pulverulent substance being subjected to a rotating movement in such an amount that the point of equilibrium between the moisture content of the substance and that of the air is exceeded, and subsequently drying this moist substance until its moisture content falls to or below this point of equilibrium.

5 Claims, No Drawings

PROCESS FOR THE PRODUCTION OF GRANULES

The invention relates to a process for the production of granules, as well as to the granules, as an industrial product, obtained by the process.

It is known that granules are formed as a result of a mixing and tumbling agitation of the material in the presence of, or with the application of, small amounts of a liquid phase. See, e.g., the article by H. B. Ries: "Aufbaugranulierung" (Build-up granulation) in 'Aufbereitungstechnik' (Preparation techniques) - No. 11/1971, page 675 ff.

It has now been found that with an excess addition of the liquid phase and subsequent drying of the granules, as a result of which the excess liquid phase is removed, there are obtained granules which, compared with the granules obtained by the initially mentioned method, surprisingly have an improved mechanical stability, a homogeneous particle size and an improved solubility or dispersibility. In this manner it is possible in particular to convert very dusty fine powder into a non-dusty or negligibly dusty granular form.

The invention hence relates to an improved process for the production of granules, comprising application of a granulating liquid to a pulverulent substance being subjected to a rotating movement in such an amount that the point of equilibrium between the moisture content of the substance and that of the air is exceeded; and subsequently drying this moist substance until its moisture content falls to or below this point of equilibrium.

The point of equilibrium between the moisture content of the substance and that of the air is the amount of moisture of the pulverulent substance when the partial vapor pressure of the moisture of the pulverulent substance corresponds to the partial vapor pressure of the surrounding atmosphere.

These combined measures, namely application of excess granulating liquid and subsequent removal thereof by drying, are new and constitute the aforementioned advance in the art.

As the pulverulent substance, any inorganic or organic substance is suitable, and either homogeneous substances or mixtures of substances can be used for the purpose.

The substances concerned are for example: dyes, pigments, optical brighteners, or textile auxiliaries, pharmaceutical products, mixtures of active substances for the manufacture of tablets, pesticidal compositions, foodstuffs and food supplements such as coffee powder, milk powder or flour; starch and starch decomposition products such as dextrin; antimicrobics and bacteriostatics; animal feeds, herbicides, plant protection products; detergents, paper auxiliaries (e.g. sizing agents), photochemicals, leather chemicals, polymers, plastics additives, synthetic resin moulding compounds, explosives, building materials, coal, ores, catalysts, chemicals, fertilisers, intermediates for cement manufacture, starting materials for ceramic products and also raw materials for powder metallurgy.

By dyes as substances are meant here all possible classes, both coloristically and chemically, which are suitable for an aqueous and organic application. Examples which may be mentioned are: basic dyes, acid dyes, sulphur dyes, vat dyes, mordant dyes, chrome dyes, disperse dyes and direct dyes, and the dyes can contain fiber-reactive groups in the molecule. It is understood that also foodstuff dyes and, for example, leather dyes are included.

Suitable chemical classes of dyes are e.g. nitroso, nitro, monoazo, disazo, trisazo, polyazo, stilbene, carotenoid, diphenylmethane, triarylmethane, xanthene, acridine, quinoline, methine, thiazole, indamine, indophenol, azine, oxazine, thiazine, lactone, aminoketone, hydroxyketone, anthraquinone, indigoid and phthalocyanine dyes, as well as 1:1- or 1:2-metal-complex dyes.

Suitable optical brighteners, which are used for white tinting, can be of any class of brighteners; for example, they are, stilbene compounds such as cyanuric derivatives of 4,4'-diaminostilbene-2,2'-disulphonic acid or distyrylbiphenyls, coumarins, benzocoumarins, pyrazines, pyrazolines, oxazines, mono- or dibenzoxazolyl, mono- or dibenzimidazolyl compounds as well as naphthalic acid imides or naphthotriazole and v-triazole derivatives.

By textile auxiliaries are meant chemicals that are required in the processing of the various textile fibres into finished fabrics, such as raw-wool detergents, lubricants, sizing agents, milling agents, impregnating agents, preserving agents, finishing agents desizing agents, kier-boiling agents. bleaching auxiliaries, dyeing auxiliaries such as dispersing agents and levelling agents, printing auxiliaries, carbonising auxiliaries, mercerising auxiliaries, preparations for producing resistance to creasing and to shrinking, and antistatic preparations.

Pesticidal compositions are in general known. They are used, for example, to destroy plant pests (e.g. fungicides, insecticides, acaricides, nematicides, molluscicides and rodenticides), and to prevent plant diseases.

Antimicrobics are antimicrobial substances which are intended to, or serve to, retard or prevent disadvantageous changes caused by microorganisms in foodstuffs.

Bacteriostatics are substances which inhibit or prevent the growth of bacteria.

By detergents are meant those substances which are composed of, for example, (a) a synthetic detergent substance, a detergent basic material; (b) a washing assistant (scouring additive); (c) special additives such as sodium perborate, magnesium silicate, optical bleaching agents, wetting agents, etc; and (d) extenders. Both the detergents as such and the individual constituents can be granulated according to the invention.

Finally, polymers can be granulated, by which are meant macromolecular organic compounds which are obtained by transformation of natural products or by synthesis, and which also include plastic materials.

The pulverulent substance can be a pure substance or a diluted substance. It is also possible to use as the pulverulent substance a material that has already been spray dried.

The granulating liquid is preferably water or an organic liquid, e.g. liquid alcohols, which can optionally contain additives in amounts of 0.1 to 50% by weight, relative to the granulating liquid. This multicomponent granulating liquid is a homogeneous solution or emulsion and is obtained by introducing the additives to the granulating liquid and stirring this until it is homogeneous.

Suitable such additives are, for example: wetting and dispersing agents of anionic, cationic or nonionic nature, such as lignin sulphonate, dinaphthylmethanedisulphonic acid, sodium-dioctyl-sulphosuccinate, dibutylnaphthalenesulphonate, dodecylbenzenesulphonate, laurylpyridinium chloride, alkylphenolpolyglycol ether, stearyl-diphenyl-oxethyldiethylenetriamine and ethylene oxide adducts; then binders such as dextrin, saccharose, starch, alginates, gelatine, glycerin, glycols, carboxymethylcellulose, polyvinylpyrrolidones, polyvinyl alcohols, a mixture of mineral sulphonic acid and an emulsifier (Essotex), polyoxypropylene glycols (block polymers of polyethylene oxide with polypropylene glycol), ethylene carbonate, or a mixture of paraffin oil and a nonionic emulsifier; as well as agents improving solubility, such as urea, tetramethylurea, caprolactam, polyethylene glycols, and diluting agents such as sodium chloride and sodium sulphate.

The process is carried out by subjecting the pulverulent substance to, in particular, a tumbling or rolling motion at room temperature, for example in a rotating drum (granulating drum). To this tumbling or rolling substance is then applied the granulating liquid, which is at a temperature of about 10 to 80° C., especially 15 to 25° C., for example by means of spraying through a fine spraying nozzle or through a coarser spraying nozzle, and in this respect it has to be ensured that on the one hand the substance becomes uniformly wetted and that on the other hand the droplet diameter in the case of a fine spraying nozzle is preferably between about $10\mu$ and $300\mu$ in order to attain a homogeneous particle size of the granulate, whereby $1\mu = 1$ micron $= 1/1000$ mm. The amount of granulating liquid used is such that the equilibrium value of the sorption of water vapour by the pulverulent substance at the ambient temperature and pressure is exceeded, with the amount of excess liquid thus applied, depending on the substance employed, being about 5 to 300%, preferably from 5 to 40% by weight, relative to the amount of substance.

This excess amount of liquid is subsequently dried off until the moisture content of the substance falls to or below the point of equilibrium between the moisture content of the substance and that of the air, e.g. in a drying apparatus, such as in a fluidised bed dryer.

By this process, the agglomeration of the primary powder particles of the substance is initiated by the applied liquid and intensified by the tumbling or rolling movement resulting from the rotation of the drum.

The process is particularly suitable therefore also for spray-dried powders, since there is obtained by this process an improvement of the dust behaviour, of the dissolving behaviour (wetting, solubility) and of the flowability, compared with these properties of the spray-dried material. Furthermore, the process is particularly suitable for use with hygroscopic substances.

By virtue of the excess amount of granulating liquid, the surface of the particles of the substance becomes in the ideal case dissolved and a bonding action is thus created between the particles, so that generally no further additives, in particular binders, need to be added to the granulating liquid.

The agglomerate strength is influenced mainly by the properties of the applied granulated liquid, and is based on a solid or liquid bridging bond between the primary particles of powder.

There are obtained by the process according to the invention negligibly dusty to non-dusty granules having a particle size of about 500 to $2000\mu$, which are characterised by a homogeneous, dimensionally stable particle size, by a high mechanical strength, by their flowability and by their good dissolving behaviour, such as wetting, dispersibility and solubility rate. In particular, they form no dust during transport and processing.

The process according to the invention is particularly suitable for the production of granulates from substances which are sensitive to heat, since the process may be carried out under mild conditions. Especially sensitive substances may be dried for a longer time at a lower temperature.

The granules obtained by the process according to the invention can contain, besides solid and liquid, high-boiling additives which are applied with the granulating liquid, also small proportions of granulating liquid, with the proportion of this being of the order of magnitude of the moisture content of the pulverulent starting materials.

The following Examples illustrate the invention without this being limited to them. The temperatures are given in degrees Centigrade.

The substances given in the Examples are employed, where not specified otherwise, in the usual commercial form containing the usual diluents. The water content of the moist granules consists of the amount of liquid which has been applied by spraying in addition to the moisture content of the starting substance.

EXAMPLE 1

100 g of the dry, non-dusty dye of the formula

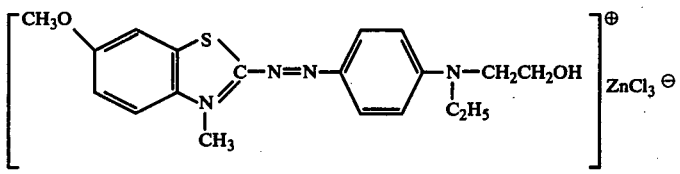

is placed as powder into an agglomerating drum of 20 cm diameter and 20 cm in length, and the drum is then rotated (25 r.p.m.).

50 g of a granulating liquid of the composition:
85% of water,
10% of polyoxypropylene glycol and
5% of an adduct of stearyldiphenyloxethyldiethylenetriamine and ethylene oxide
is mixed together in a beaker and stirred with a magnetic stirrer for 10 minutes to form a homogeneous solution.

The granulating liquid is smoothly fed into the spray nozzles by means of a squeeze tube pump. With a throughput of liquid of 6 g/minute, the two-component nozzle is adjusted to give a droplet size of 10 to $100\mu$ with a suitable spray cone. The nozzle is inserted through the lateral drum opening into the drum, and the agitated dye powder is uniformly sprayed for 1.7 minutes. The nozzle is subsequently removed from the drum, and the moistened, agglomerated powder is after-tumbled for about one minute further.

110 g of the moist agglomerate is transferred to the fluidised bed dryer and dried at an air temperature of 90 to 100° for 4 minutes. The rate of flow in the empty tube is about 0.4 m/sec. at an air temperature of 100°. Any fine particles present or fine powder formed during drying is separated in the cyclone separator located on the output side and can be fed back for subsequent agglomeration. The moisture content of the agglomerate leaving the drum was 9.5%, whereas the dried agglomerated product has a water content of 1%.

There is obtained about 100 g of negligibly dusty, flowable and dimensionably stable dye granules of the composition:
97.5% of the above dye,
1.0% of polyoxypropylene glycol,
0.5% of an adduct of stearyldiphenyloxethyldiethylenetriamine and ethylene oxide, and
1.0% of water,
which granules retain on storage in air their nature and shape.

Compared with the dye powder, the dye granules have better wettability and hence also have a good dissolving capacity.

Granules of the composition given in the following Examples 2 to 16 are obtained by using the constituents and operating conditions stated in these Examples, but otherwise employing the procedure according to Example 1.

EXAMPLE 2

Substance: dye mixture of the dyestuffs of the formulae

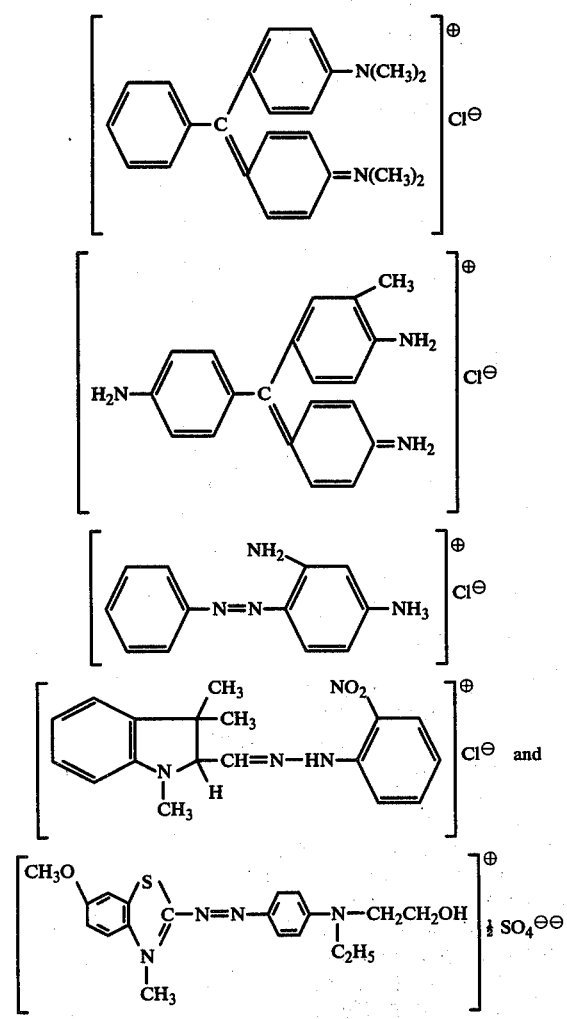

amount of mixture used: 100 g;
granulating liquid:
  composition:
    75% by weight of water,
    25% by weight of a mixture of paraffin oil and nonionic emulsifier;
  amount: 9 g;
length of time in drum: 2.5 minutes;
water content of the moist granules: 8.4%;
drying temperature: 90 to 100°;
length of time in dryer: 3 minutes;
composition of granules:
  96.0% by weight of dye mixture,
  2.2% by weight of a mixture of paraffin oil and nonionic emulsifier,
  1.8% by weight of water.

EXAMPLE 3

Substance: dye of the formula

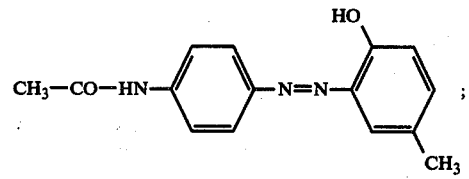

amount of dye used: 100 g;
granulating liquid:
  composition:
    40% by weight of dextrin,
    10% by weight of polyoxypropylene glycol,
    50% by weight of water;
  amount: 30 g;
length of time in drum: 6 minutes;
water content of the moist granules: 13.4%;
drying temperature: 90 to 100°;
length of time in dryer: 7 minutes;
composition of granules:
  84.0% by weight of dye,
  10.1% by weight of dextrin,
  2.5% by weight of polyoxypropylene glycol,
  3.5% by weight of water.

EXAMPLE 4

Substance: dye mixture of

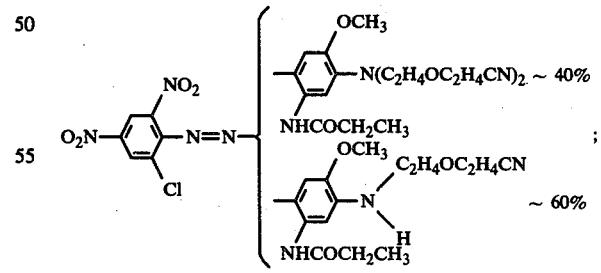

amount of dye mixture used: 100 g;
granulating liquid:
  composition:
    95% by weight of water,
    5% by weight of lignin sulphonate;
  amount: 30 g;
length of time in drum: 6 minutes;
water content of the moist granules: 25.0%;

drying temperature: 90 to 100°;
length of time in dryer: 11 minutes;
composition of granules:
  93.0% by weight of dye mixture,
  1.2% by weight of lignin sulphonate,
  5.8% by weight of water.

EXAMPLE 5

Substance: dye of the formula

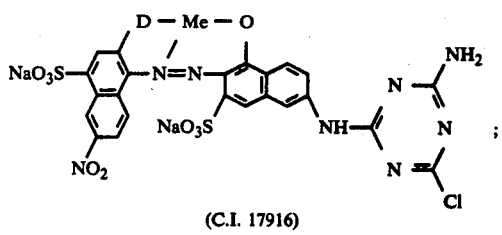

(C.I. 17916)

amount of dye used: 300 g;
granulating liquid:
  composition:
    70% by weight of water,
    20% by weight of dextrin,
    10% by weight of a mixture of mineral sulfonic acid and emulsifier;
  amount: 90 g;
length of time in drum: 16 minutes;
water content of the moist granules: 17.4%;
drying temperature: 100 to 120°;
length of time in dryer: 20 minutes;
composition of granules:
  90.4% by weight of dye,
  5.4% by weight of dextrin,
  2.7% by weight of a mixture of mineral sulphonic acid and emulsifier,
  1.5% by weight of water.

EXAMPLE 6

Substance: dye of the formula

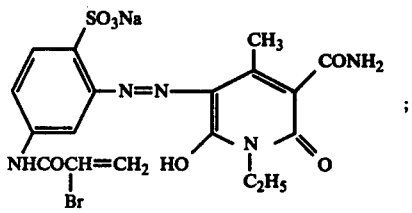

amount of dye used: 100 g;
granulating liquid:
  composition:
    65% by weight of water,
    35% by weight of a mixture of mineral sulphonic acid and emulsifier,
  amount: 15 g;
length of time in drum: 3.5 minutes;
water content of the moist granules: 13.8%; drying temperature: 90 to 110°;
length of time in dryer: 4 minutes;
granulating composition:
  92.5% by weight of the dye,
  4.9% by weight of a mixture of mineral sulphonic acid and emulsifier,
  2.6% by weight of water.

EXAMPLE 7

Substance: dye of the formula 1:2 chrome complex of

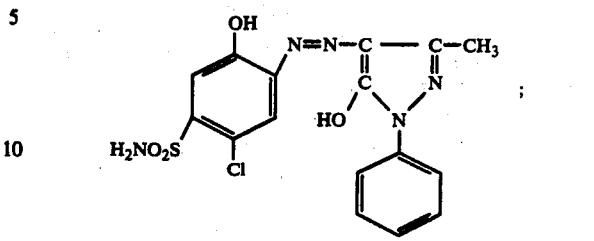

amount of dye used: 250 g;
granulating liquid:
  composition:
    80% by weight of water,
    20% by weight of a mixture of mineral sulphonic acid and emulsifier,
  amount: 100 g;
length of time in drum: 13.5 minutes;
water content of the moist granules: 26.3%;
drying temperature: 90 to 110°;
length of time in dryer: 20 minutes;
composition of the granules:
  91.2% by weight of dye,
  7.3% by weight of a mixture of mineral sulphonic acid and emulsifier,
  1.5% by weight of water.

EXAMPLE 8

Substance: dye of the formula

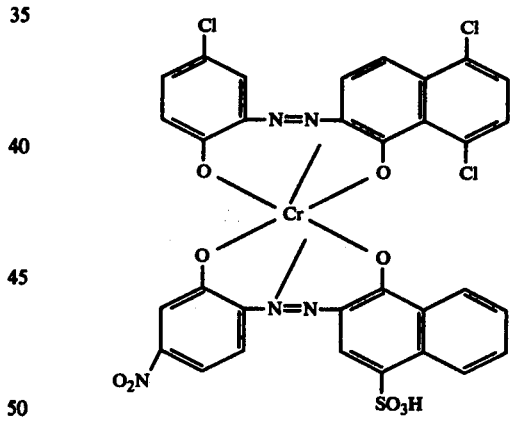

amount of dye used: 500 g;
granulating liquid:
  composition:
    70% by weight of water,
    20% by weight of dextrin,
    5% by weight of polyvinyl alcohol,
    5% by weight of a mixture of mineral sulphonic acid and emulsifier,
  amount: 240 g;
length of time in drum: 20 minutes;
water content of the moist granules: 26.7%;
drying temperature: 100 to 120°;
length of time in dryer: 28 minutes;
composition of the granules:
  85.2% by weight of dye,
  8.2% by weight of dextrin,
  2.1% by weight of polyvinyl alcohol, 2.1% by weight of a mixture of mineral sulphonic acid and emulsifier,
2.4% by weight of water.

EXAMPLE 9

Substance: dye of the formula

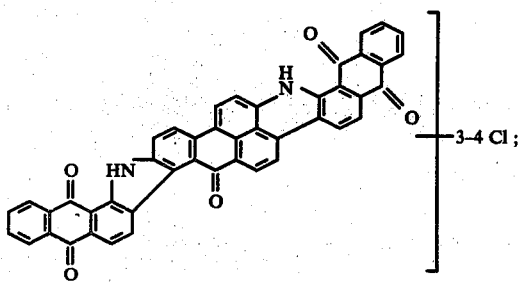

amount of dye used: 500 g;
granulating liquid:
 composition:
  80% by weight of water,
  20% by weight of a mixture of mineral sulphonic acid and emulsifier,
 amount: 125 g;
length of time in drum: 20 minutes;
water content of the moist granules: 20.0%;
drying temperature: 90 to 100°;
length of time in dryer: 18 minutes;
composition of the granules:
 93.0% by weight of dye,
 4.7% by weight of a mixture of mineral sulphonic acid and emulsifier,
 2.3% by weight of water.

EXAMPLE 10

Substance: dye of the formula

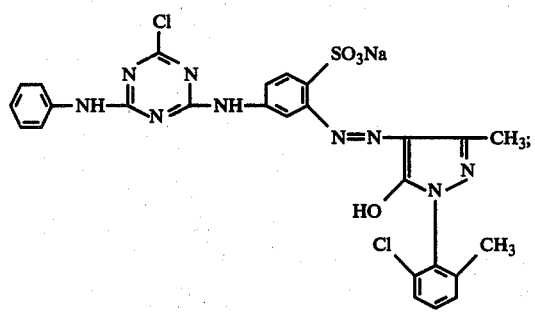

amount of dye used: 100 g;
granulating liquid:
 composition:
  70% by weight of water,
  10% by weight of a mixture of mineral sulphonic acid and emulsifier,
  20% by weight of dextrin;
 amount: 36 g;
length of time in drum: 11 minutes;
water content of the moist granules: 21.3%;
drying temperature: 100 to 120°;
length of time in dryer: 5 minutes;
composition of the granules:
 84.3% by weight of dye,
 6.1% by weight of dextrin,
 3.0% by weight of a mixture of mineral sulphonic acid and emulsifier,
 6.6% by weight of water.

EXAMPLE 11

Substance: dye composed of the condensation product of p-nitrotoluenesulphonic acid with sodium hydroxide solution;
amount of dye used: 100 g;
granulating liquid:
 composition:
  75% by weight of water,
  20% by weight of dextrin,
  5% by weight of a mixture of mineral sulphonic acid and emulsifier,
 amount: 30 g;
length of time in drum: 7 minutes;
water content of the moist granules: 19.8%;
drying temperature: 110 to 120°;
length of time in the dryer: 5 minutes;
composition of the granules:
 91.6% by weight of dye,
 5.5% by weight of dextrin,
 1.4% by weight of a mixture of mineral sulphonic acid and emulsifier,
 1.5% by weight of water.

EXAMPLE 12

Substance: optical brightener of the formula

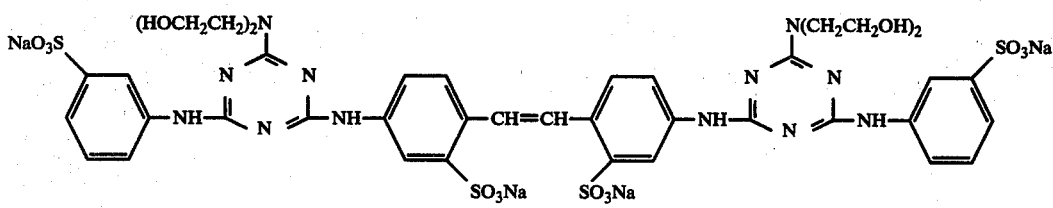

amount of optical brightener used: 100 g;
granulating liquid:
 composition:
  80% by weight of water,
  20% by weight of alkylphenolpolyglycol ether;
 amount 42 g;
length of time in drum: 8 minutes;
water content of the moist granules: 26.9%;
drying temperature: 90° to 110°;
length of time in dryer: 7 minutes;
composition of granules:
 87.8% by weight of optical brightener,
 7.4% by weight of alkylphenolpolyglycol ether,
 4.8% by weight of water.

EXAMPLE 13

Substance: synthetic detergent of the formula

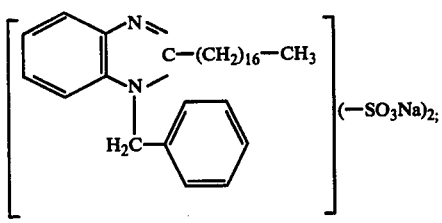

amount of synthetic detergent used: 500 g;
granulating liquid:
  composition: 100% by weight of water
  amount: 54 g;
length of time in drum: 21 minutes;
water content of the moist granules: 12.1%;
drying temperature: 90° to 110°;
length of time in dryer: 20 minutes;
composition of the granules:
  99.4% by weight of synthetic detergent,
  0.6% by weight of water.

EXAMPLE 14

Substance: (plastics additive)

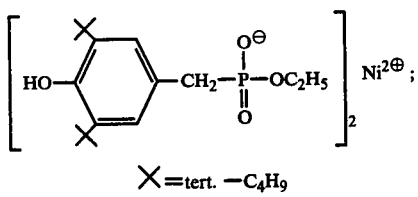

X = tert. —C₄H₉ amount of substance used: 100 g;
granulating liquid:
  composition:
    80% by weight of water,
    20% by weight of paraffin oil;
  amount: 30 g;
length of time in drum: 6 minutes;
water content of the moist granules: 19.7%;
drying temperature: 90° to 100°;
length of time in dryer: 5 minutes;
composition of the granules:
  92.9% by weight of the above substance,
  5.6% by weight of paraffin oil,
  1.5% by weight of water.

EXAMPLE 15

Substance: dextrin (pure substance, no additives);
amount of dextrin used: 200 g;
granulating liquid:
  composition: 100% by weight of water;
  amount: 9 g;
length of time in drum: 3 minutes;
water content of the moist granules: 12.9%; drying temperature: 50° to 60°;
length of time in dryer: 6 minutes;
composition of granules:
  93.5% by weight of dextrin,
  6.5% by weight of water.

EXAMPLE 16

Substance: wheat flour (pure product, no additives);
amount of wheat flour used: 100 g;
granulating liquid:
  composition: 100% by weight of water;
  amount: 20 g;
length of time in drum: 4.3 minutes;
water content of the moist granules: 26.7%;
drying temperature: 90° to 110°;
length of time in dryer: 6 minutes;
composition of the granules:
  95.5% by weight of wheat flour,
  4.5% by weight of water.

EXAMPLE 17

Substance: dye of the formula

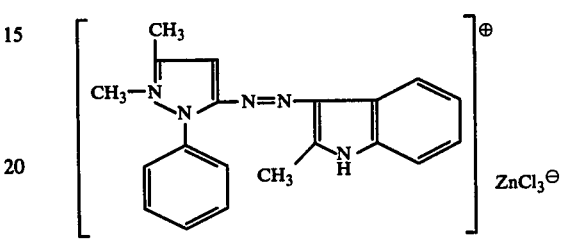

amount of dye used: 500 g;
granulating liquid:
  composition:
    70% by weight of water,
    20% by weight of dextrin,
    10% by weight of a mixture of mineral acid and emulsifier;
  amount:
    115 g;
length of time in drum: 20 minutes;
water content of the moist granules: 20.0%;
drying temperature: 65° to 75°;
length of time in dryer: 18 minutes;
composition of the granules:
  90.5% by weight of dye,
  4.6% by weight of dextrin
  2.3% by weight of the mixture of mineral acid and emulsifier,
  2.6% by weight of water.

EXAMPLE 18

Substance: dye of the formula

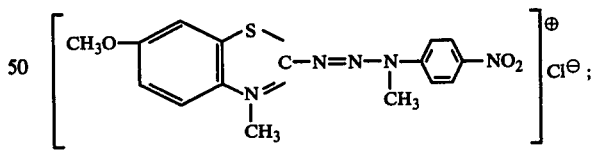

amount of dye used: 500 g;
granulating liquid:
  composition:
    50% by weight of water,
    50% by weight of ethylene carbonate;
  amount:
    70 g;
length of time in drum: 13 minutes;
water content of the moist granules: 10.3%;
drying temperature: 50° to 60°;
length of time in dryer: 16 minutes;
composition of the granules:
  86.4% by weight of dye,
  6.0% by weight of ethylene carbonate

EXAMPLE 19

Substance: dye of the formula

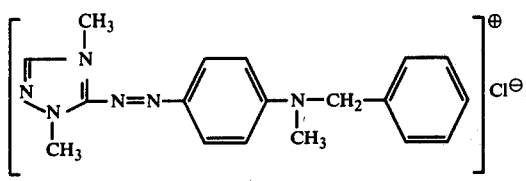

amount of dye used: 300 g;
granulating liquid:
  composition:
    50% by weight of water,
    50% by weight of ethylene carbonate;
  amount:
    55 g;
length of time in drum: 10 minutes;
water content of the moist granules: 17.3%;
drying temperature: 60° to 70°;
length of time in dryer: 14 minutes;
composition of the granules:
  85.9% by weight of dye,
  7.9% by weight of ethylene carbonate,
  6.2% by weight of water.

EXAMPLE 20

Substance: dye mixture of the formulae

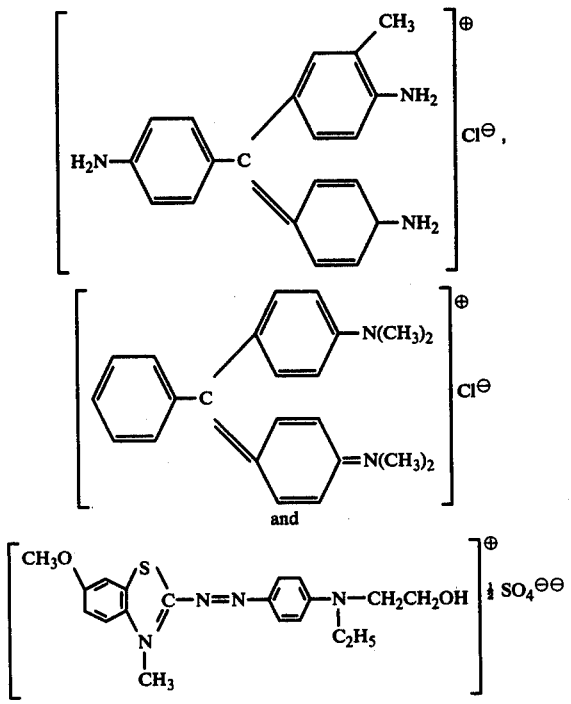

amount of dye used: 500 g;
granulating liquid:
  composition:
    60% by weight of water,
    30% by weight of alkylphenol polyglycol ether,
    10% by weight of a mixture of paraffin oil and nonionic emulsifier;
  amount: 33 g;
length of time in drum: 6.5 minutes;
water content of the moist granules: 6.9%;
drying temperature: 70° to 80°;
length of time in dryer: 8 minutes;
composition of the granules:
  96.6% by weight of dye,
  1.9% by weight of alkylphenol polyglycol ether,
  0.7% by weight of the mixture of paraffin oil and nonionic emulsifier,
  0.8% by weight of water.

EXAMPLE 21

Substance: herbicide of the formula

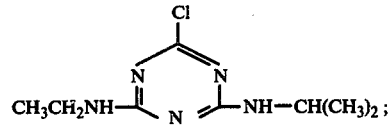

amount of herbicide used: 100 g;
granulating liquid:
  composition: 100% by weight of water.
  amount: 20 g;
length of time in drum: 6 minutes;
water content of the moist granules: 18.0%;
drying temperature: 70° to 85°;
length of time in dryer: 5 minutes;
composition of the granules:
  99.2% by weight of herbicide,
  0.8% by weight of water.

We claim:

1. A solid granulate consisting essentially of 45 to 99.5% by weight of an organic substance and 0.1 to 50% by weight of additives and the remainder moisture, manufactured by a process comprising the steps of
   (a) applying a granulating liquid, containing 0.1 to 50% by weight relative to the granulating liquid of at least one granulating assistant selected from the group consisting of a wetting agent, a dispersing agent, a binding agent and a solubility improving agent, to a pulverulent organic substance, which is subjected to a tumbling or rolling rotating movement, said granulating liquid being applied to such an amount that the point of equilibrium between the moisture content of the substance and that of the air is exceeded, and is from 5% to 300% by weight relative to the pulverulent substance, to uniformly moisten said pulverulent organic substance and dissolve the surface of the particles of the substance, thereby forming a moist granulate thereof; and
   (b) subsequently drying the moist granulate until its moisture content falls to or below said point of equilibrium to form said solid granulate.

2. The granulate according to claim 1, wherein the pulverulent substance is a dyestuff.

3. The granulate according to claim 1, wherein the pulverulent substance is selected from the group consisting of a pigment, an optical brightener, a textile auxiliary, a synthetic detergent, a plastics additive and a polymeric substance.

4. The granulate according to claim 1, wherein the pulverulent substance is selected from the group consisting of an animal feed, a pesticide, a plant protection product and a herbicide.

5. The granulate according to claim 1, wherein the pulverulent substance is selected from the group consisting of a pharmaceutical product, an antimicrobic and bacteriostatic substance.

* * * * *